United States Patent [19]

Grendol et al.

[11] Patent Number: 4,810,080
[45] Date of Patent: Mar. 7, 1989

[54] PROTECTIVE EYEWEAR WITH REMOVABLE NOSEPIECE AND CORRECTIVE SPECTACLE

[75] Inventors: Clark L. Grendol, Sturbridge; Arlene J. Philla, W. Boylston, both of Mass.

[73] Assignee: American Optical Corporation, Southbridge, Mass.

[21] Appl. No.: 92,488

[22] Filed: Sep. 3, 1987

[51] Int. Cl.⁴ .......................... G02C 5/12; G02C 1/00
[52] U.S. Cl. ...................... 351/41; 351/138; 351/158; 351/88
[58] Field of Search ............... 351/41, 60, 63, 158, 351/138, 88; 2/444

[56] References Cited

U.S. PATENT DOCUMENTS

| | | |
|---|---|---|
| 1,230,555 | 6/1917 | Brennecke . |
| 2,905,172 | 9/1959 | Rodenhouse . |
| 4,542,965 | 9/1985 | Shedrow . |
| 4,711,539 | 12/1987 | Krusas et al. ................ 351/41 X |

FOREIGN PATENT DOCUMENTS 1171750 12/1960 Fed. Rep. of Germany .
2419526 11/1979 France ................................ 351/138

OTHER PUBLICATIONS

"The Industrial Smoke Spec Safety Spectacle" Scuba Spec. Inc.
J. Krusas et al., Ser. No. 746,178 (filed 6-18-85).

Primary Examiner—Rodney B. Bovernick
Attorney, Agent, or Firm—Fishman, Dionne & Cantor

[57] ABSTRACT

A universal fit protective spectacle and assembly kit therefor are disclosed. The protective spectacle is especially adapted for use by eyeglass wearers since it includes an inner spectacle that holds corrective lenses removably mounted to an outer protective spectacle. The protective spectacle also includes removably mountable and interchangable nosepieces of various sizes to achieve a comfortable fit.

35 Claims, 3 Drawing Sheets

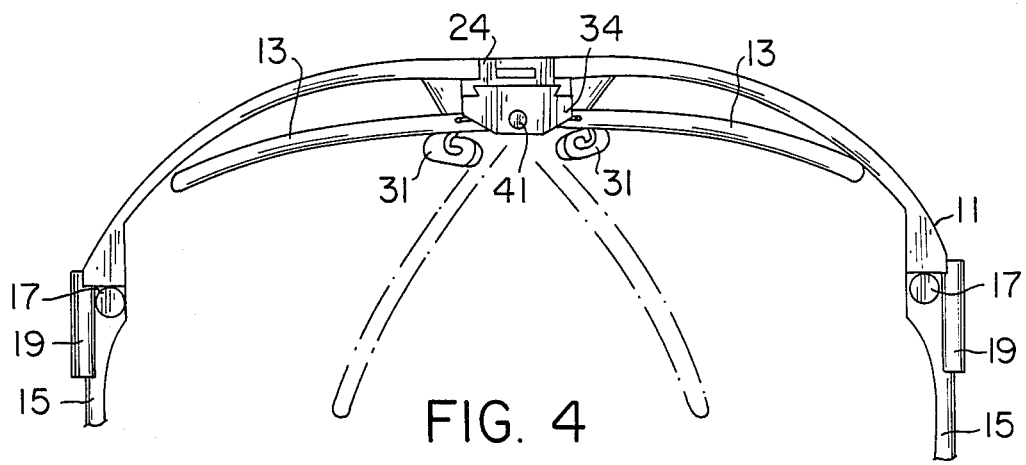
FIG. 4
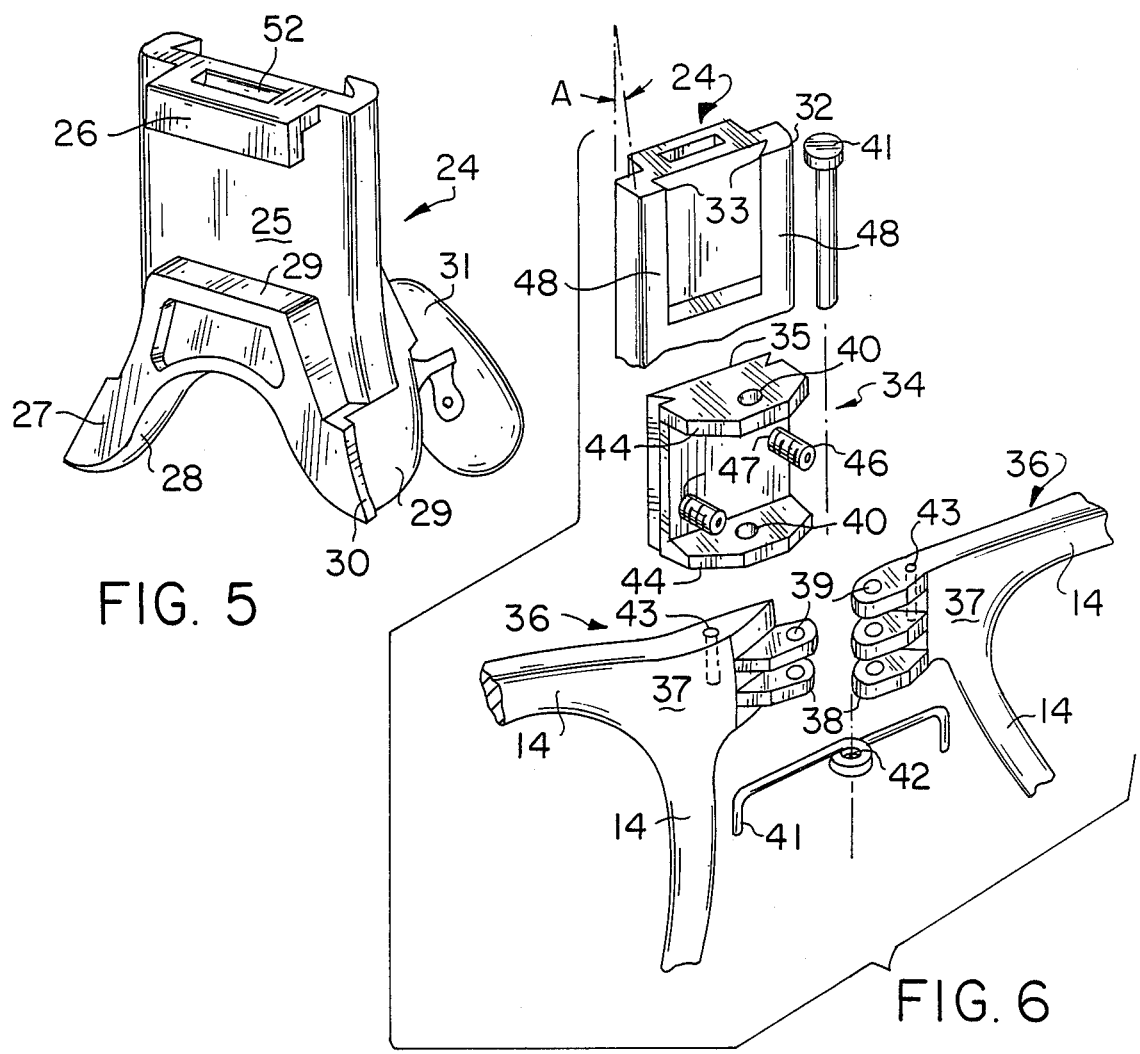
FIG. 5
FIG. 6

PROTECTIVE EYEWEAR WITH REMOVABLE NOSEPIECE AND CORRECTIVE SPECTACLE

BACKGROUND OF THE INVENTION

This invention relates to protective spectacles and particularly to protective spectacles for a wearer requiring vision correction.

People working in potentially hazardous work environments generally require protective spectacles (or goggles) to protect their eyes from projectiles. Those people who wear corrective eyeglasses require special attention in fitting protective spectacles since consideration must be given to their need to maintain vision correction in addition to providing optimum protection. Heretofore their needs have been met by providing a pair of impact resistant corrective eyeglasses, generally with sideshields, or by providing a protective spectacle which is large enough to fit over the corrective eyeglasses. Either arrangement is less than ideal.

In the former case, individual impact-resistant eyeglasses must be made-up for each wearer which is an expensive, time-consuming process. If the specially made eyeglasses are scratched, worn or damaged, new ones must be made-up. If protection against a variety of hazards is required, then several pairs of eyeglasses may be required, one pair for each type of hazard to be encountered. In the latter case, it is sometimes difficult to find a protective spectacle which fits comfortably on the wearer and fits over the wearer's corrective eyeglasses, which can vary in size and shape. The fit is often cumbersome and sloppy.

In view of the above-described disadvantages it would be highly desirable to make available a universal protective spectacle that can be inexpensively produced and worn by both eyeglass wearers and non-eyeglass wearers alike. Such a protective spectacle should be adaptable to meet a variety of hazards and enable the eyeglass wearer to utilize only one pair of corrective lenses regardless of wear or damage to the protective spectacle or the hazard encountered.

SUMMARY OF THE INVENTION

The present invention provides a universal fit protective spectacle and an assembly kit therefor. The protective spectacle comprises an outer protective spectacle which may be worn by non-eyeglass wearers or by eyeglass wearers when an inner spectacle, which holds corrective lenses, is mounted thereon. The outer protective spectacle comes equipped with replaceable nosepieces of various sizes to achieve an optimum fit. The inner spectacle may be utilized with outer protective spectacles designed to meet a variety of hazards, as well as with other types of protective equipment.

BRIEF DESCRIPTION OF THE DRAWINGS

FIG. 4 is a partial plan view of the protective spectacle shown in FIG. 1.

FIG. 5 is an enlarged front isometric view of the nosepiece utilized with the protective spectacle shown in FIG. 1.

FIG. 6 is an exploded partial isometric view of the inner spectacle utilized with the protective spectacle shown in FIG. 1, including a partial rear isometric view of the nosepiece shown in FIG. 5.

DETAILED DESCRIPTION OF THE PREFERRED EMBODIMENTS

Figure 1:
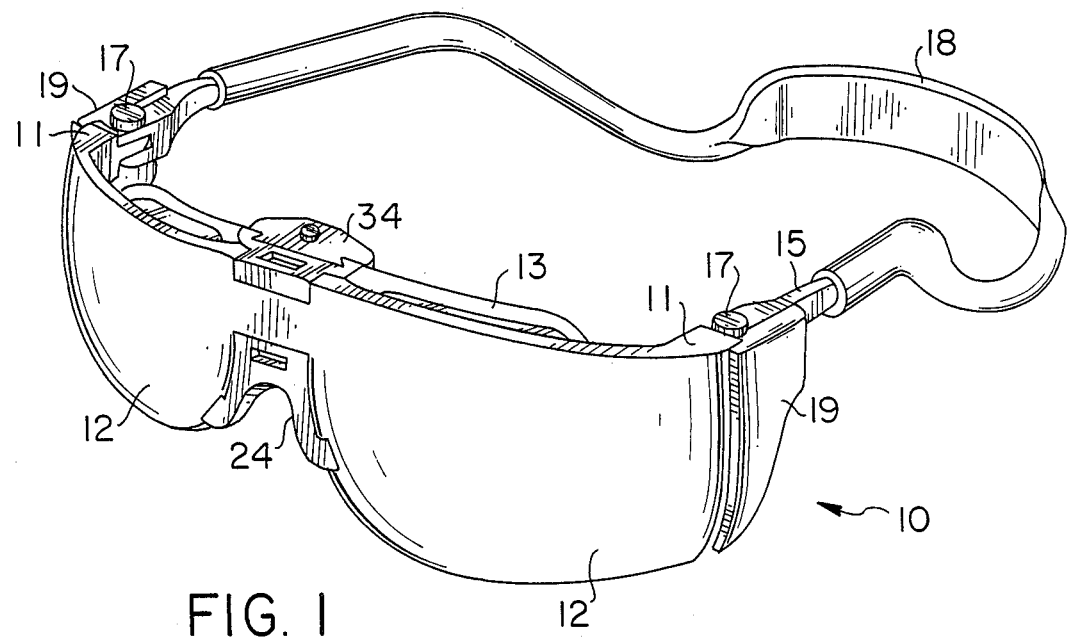
FIG. 1 is a front isometric view of the protective spectacle of the present invention.

The present invention is best understood with reference to the above-described drawings, wherein like elements are referred to by like reference numerals.

With reference to FIGS. 1-4, the present invention in its simplest form comprises a protective spectacle 10, or an assembly kit therefor, comprising an outer impact resistant, visually-transparent protective spectacle 11 structured to fit the face of the wearer and be retained thereon at eye level so as to substantially protect the eyes of the wearer from projectiles, and an inner spectacle 13 adapted to hold corrective lenses (such as in lens defining portions 14), said inner spectacle being mounted to the inner side of said outer protective spectacle such as to be positioned between the outer protective spectacle and the eyes of the wearer in a position to afford optimum visual correction.

Optimum vision correction is normally achieved when the inner spectacle is mounted at approximately the optimum vertex position (i.e. the vertical position of the lens centers with respect to the pupils), face-form angle (i.e. the angle defined by the intersection of the planes formed through the perimeters of the corrective lenses), and pantoscopic angle (i.e. the angle by which the vertical axis of the corrective lens is inclined to a nominal reference with respect to the wearer's face).

The outer protective spectacle may have temple members 15 hingedly attached at the outer extremities thereof and extending rearwardly therefrom to engage the head and ears of the wearer. While any conventional attachment of the temple members is appropriate, it is advantageous to utilize molded-in mating hinge members 16 at the outer extremities of the outer protective spectacle and on the temple members, which can be joined and retained with manually insertable hinge pins 17. Optionally, head band 18 may be removably attached to said temple members to assist retention of the protective spectacle on the head of the wearer, or the head band may be directly attached to the outer protective spectacle (e.g. at the hinge members) when no temples are utilized using any available attaching means. Also optional are side shields 19 which are removably attachable to said temple members and abut said outer protective spectacle, when said temples are open, preventing penetration of projectiles from the side. Sideshields may also optionally be molded as part of the outer protective spectacle if desired.

The outer protective spectacle is preferably a one-piece molded transparent or semi-transparent impact resistant plastic, most preferably of a wrap-around design to substantially protect the eyes of the wearer from projectiles. This outer protective spectacle comprises two plano lens portions 12 interconnected through a bridge portion 20 and embodies a nose bridge portion defined by the bottom edge 21 of said bridge portion and the inner facing edge 22 of said lens portions. The outer protective spectacle may optionally have a notch 23 located at the upper part of said bridge portion between said lens portions, said notch serving to anchor removable nosepiece 24 and prevent sideways motion thereof after said nosepiece is mounted in place.

Nosepiece 24 can be provided in a variety of shapes and sizes that will fit a wide range of nose sizes so that the protective spectacle of the present invention can be adapted to fit most wearers by simply selecting the correct nosepiece. Generally, nosepieces would be provided in at least small, medium and large sizes. Optionally, a nosepiece may be molded as part of the outer protective spectacle to reduce the number of separate pieces that must be manufactured, but doing so reduces the flexibility of the protective spectacle encompassed by this invention.

It is preferred to utilize nosepiece 24 which is adapted to be snappably, removably attached to the outer protective spectacle at the bridge portion thereof. This nosepiece comprises a bridge-abutting portion 25 adapted to abut the bridge portion 20 of the outer protective spectacle, preferably the rear-facing surface thereof, a clip portion 26 located at the upper end of said bridge-abutting portion and adapted to clip onto the bridge portion 20 of said outer protective spectacle, preferably within optional notch 23, and a pair of arms 27 located at the lower end of said bridge abutting portion 25 and extending downwardly therefrom, generally to form an approximately horseshoe shape. The arms 27 of the nosepiece have inner surfaces 28 adapted to conform to the shape of the nose of the wearer and have outer surfaces 29 adapted to snugly engage the nose-bridge portion 21, 22 of the outer protective spectacle. The arms 27 further have a small lip 30 extending normal to each of the outer surfaces 29 so as to snappably engage the lens portions 12 of the outer protective spectacle. Nosepiece 24 is accordingly locked onto the outer protective spectacle by the combined action of the clip portion 26 preventing downward or outward movement of the nosepiece, the lips 30 and outer surfaces 29 preventing upward or outward movement of the nosepiece, the bridge abutting portion 25 preventing forward movement of the nosepiece, and the notch 23, combined with the snug-fit of the nosepiece within the nose-bridge portion 21, 22 preventing sideways or twisting movement of the nosepiece. The nosepiece may also optionally be fitted with nosepads 31 to further improve comfort and fit on the wearer.

One of the particularly advantageous features of the present invention is the mounting of inner spectacle 13 to the inner side of the outer protective spectacle so that it is positioned between the outer protective spectacle and the eyes of the wearer. The inner spectacle is adapted to hold corrective lenses within lens openings 14. Corrective lenses corresponding to the wearer's prescription may be mounted within the lens openings 14 of the inner spectacle, then the inner spectacle mounted to the outer protective spectacle to give a comfortable protective spectacle that both corrects the wearer's vision and protects the wearer against impacting projectiles. If the outer protective spectacle is worn or damaged, or a need arises to utilize a different type of outer protective spectacle (e.g. one having a clear lens or a tinted lens or one treated for infra-red absorption), the inner spectacle may be simply mounted to a new outer protective spectacle having the desired characteristics. This capability of switching the corrective inner spectacle thus avoids the need to continually supply individual corrective lenses to each wearer or to provide various types of protective eyewear each fitted with the wearer's prescription. With the present invention the wearer can be provided with one corrective inner spectacle that can be interchanged among several types of protective equipment, including various types of outer protective spectacles. One other type of protective equipment for which this inner spectacle can be interchanged is a gas mask of the type shown in copending application Ser. No. 746,178, filed June 18, 1985, now U.S. Pat. No. 4,711,539.

The inner spectacle 13 is preferably removably mounted to the bridge portion of the outer protective spectacle via mounting means such that it is in a position to afford optimum visual correction, i.e. a position approximating the optimum vertex position, face-form angle, and pantoscopic angle. The mounting means advantageously comprises a first mounting member attached to the bridge portion of the outer protective spectacle and a corresponding mating second mounting member attached to the bridge portion of the inner spectacle. Preferably one of said mounting members has a dove-tail shaped groove and the other has a corresponding, mating, dove-tail shaped projection which slidably, removably mates with the dove-tail shaped groove.

Figure 3:
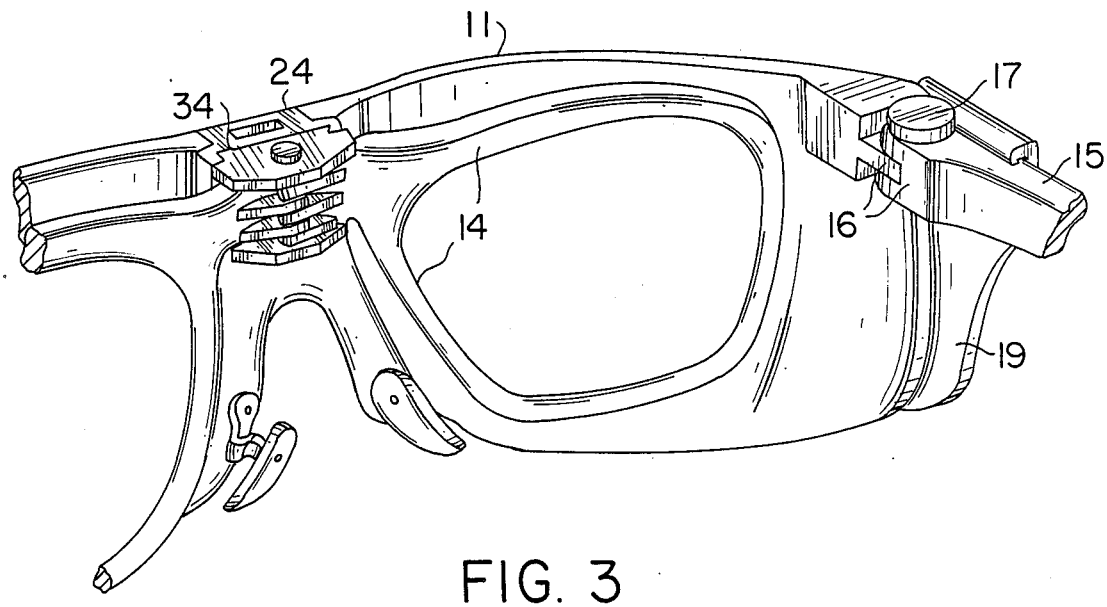
FIG. 3 is a partial rear isometric view of the protective spectacle shown in FIG. 1.
Figure 2:
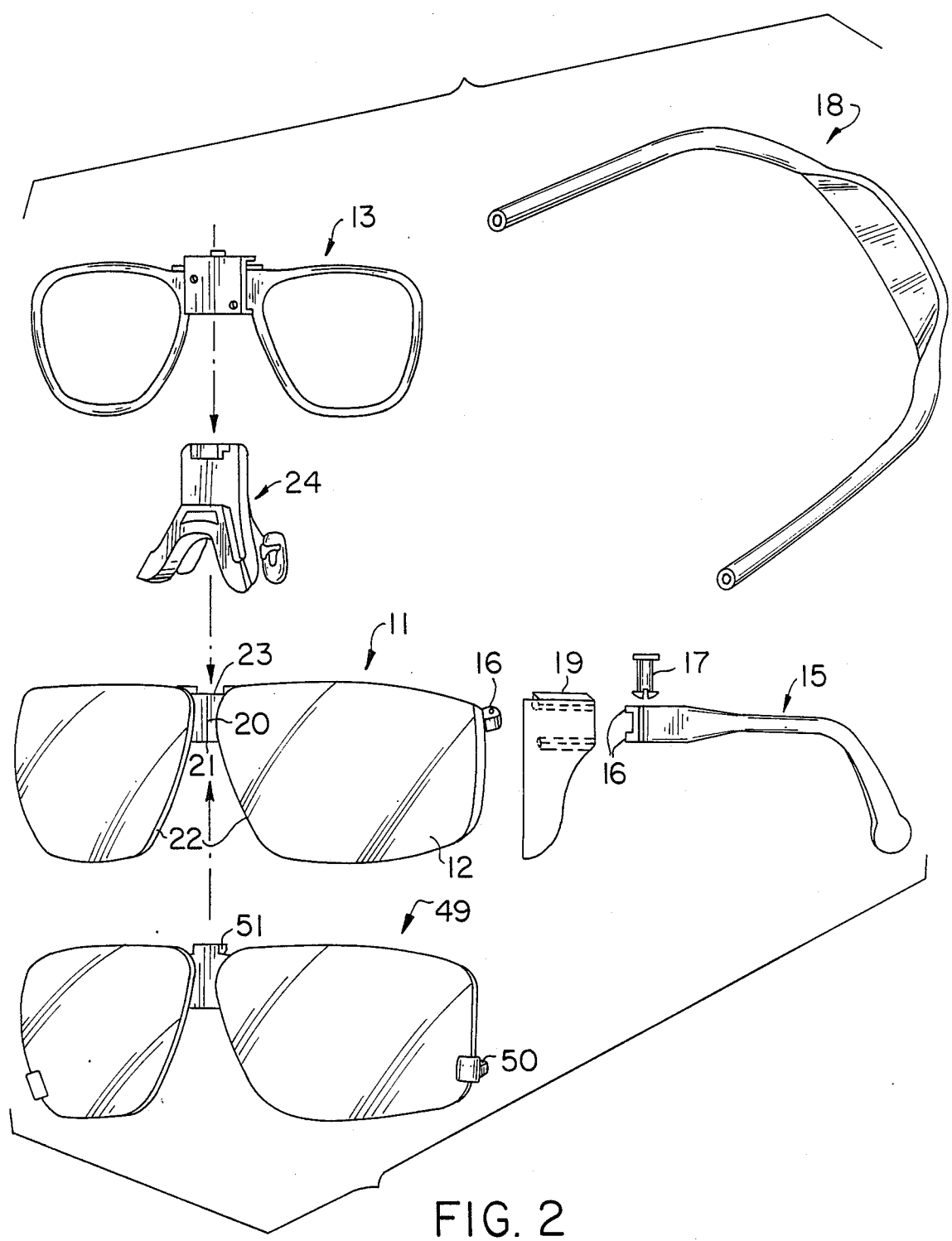
FIG. 2 is an exploded isometric view of the protective spectacle shown in FIG. 1 including an optional clip-on outer protective spectacle.

The preferred mounting of the inner spectacle to the outer protective spectacle is illustrated in Figs. 1, 3 and 4, with FIG. 6 illustrating an exploded view of the mounting means. The first mounting member 32 referred to above, which is attached to the bridge portion of the outer protective spectacle, is preferably integral with nosepiece 24 and consists of a dove-tail shaped groove 33 molded into the rear facing surface of said nosepiece, generally opposite the bridge-abutting portion 25 thereof. When the nosepiece is mounted to the bridge portion of the outer protective spectacle as described previously, first mounting member 32 is thus placed in position to matingly receive second mounting member 34.

Second mounting member 34 is one of the parts that comprise inner spectacle 13 and is positioned at the bridge portion thereof. This second mounting member has a dove-tail shaped projection 35 which is designed to fit in slideably, removably mating relation with the corresponding dove-tail shaped groove 33 in the first mounting member. When both mounting members are joined together in this fashion, the inner spectacle is thus mounted to the outer protective spectacle.

The component parts which comprise inner spectacle 13 are illustrated in exploded form in FIG. 6. As can be seen, there are two frame halves 36 each adapted to hold a corrective lens in lens defining portion 14. These frame halves are hingedly connected at their respective bridge portions 37 through mating hinge lobes 38. After mating hinge lobes 38 are fit together, torsion spring 41 is fitted into holes 43 in each of the frame halves so that loop 42 of the torsion spring is aligned with holes 39 of the mating hinge lobes 38. This subassembly may then be mounted to second mounting member 34 by sandwiching the mating hinge lobes 38 between lobes 44 of the second mounting member and inserting hinge pin 41 through holes 40, loop 42 and holes 39 of the second mounting member, torsion spring and mating hinge lobes respectively to secure the entire inner spectacle. Hinge pin 41 may be secured by threading into the lower lobe 44, by heat fusion, by ultrasonic welding, by threaded nut, by interference fit or by any other conventional technique.

The hinged assembly just described enables the two frame halves of the inner spectacle to fold inwardly toward each other as shown in phantom in FIG. 4. This feature has several advantages. It allows the corrective inner spectacle to be folded, after removal from the outer protective spectacle, and placed in a compact carrying pouch for carrying in the wearer's pocket. It enables easy manipulation of the inner spectacle for quick mounting onto the outer protective spectacle, particularly allowing the inner spectacle to fold away from the curved surface of the outer protective spectacle, thus avoiding interference between the two during installation. The hinged connection also allows the inner spectacle to be utilized in other protective equipment that requires a hinged connection, such as a folding gas mask. Of course, a hinged connection is not necessary to realize the advantages of the present invention and it is equally contemplated hereunder that the frame halves of the inner spectacle can be rigidly joined or even molded as one piece, with the second mounting member previously described joined to the bridge portion thereof in any suitable fashion. To reduce the number of separate parts, the second mounting member may also optionally be molded into the bridge portion of a one piece inner spectacle.

The inner spectacle is mounted to the outer protective spectacle by sliding the dove-tail shaped projection 35 of second mounting member 34 into dove-tail shaped groove 33 of first mounting member 32. The vertex position of the inner spectacle may be simply adjusted by sliding the second mounting member up or down with respect to the first mounting member as required. If the mating relationship between the two mounting members is snug, the second mounting member should be retained in whatever position it is adjusted to. Alternatively, optional set screws 46 may be screwed into holes 47 of the second mounting member and tightened against the first mounting member to retain or lock it in the set vertex portion.

The correct pantoscopic angle of the inner spectacle with respect to the wearer's eyes can be established by simply molding one of the mounting members in such a way that either one of said dove-tail shaped projection or groove is disposed at an angle that will enable the assembled parts to achieve the desired pantoscopic angle. In FIG. 6, the pantoscopic adjustment is illustrated as being molded into first mounting member 32 wherein the rearward face 48 thereof is disposed at an angle A with respect to the forward facing nosebridge portion 25. The dove-tail shaped groove 33 accordingly is disposed at the same angle A since it runs parallel thereto. Angle A may be set at the appropriate angle to achieve the desired pantoscopic angle when second mounting member 34 is mounted to the first mounting member.

The correct face-form angle may be molded into the inner spectacle where it is one piece. Alternatively, where there are two frame halves hingedly connected as illustrated in FIG. 6, then the respective bridge portions 37 may each be angled with respect to the lens defining portions 14 such that when the frame halves are biased open by torsion spring 41, the front surfaces of the bridge portions 37 abut the rear facing surface 45 of the second mounting member and the lens defining portions are set at the desired angle. Thus, the correct face form angle may be set by molding into each of the frame halves the correct angle between the bridge portion and the lens defining portion. Alternatively, the desired angle can be molded into rear facing surface 45 of the second mounting member.

As an optional additional component of the protective spectacle of the present invention, one may advantageously employ outer shield 49 (illustrated in FIG. 2) which is approximately the same size and shape as the outer protective spectacle 11 and is adapted to be removably retained on the outer surface thereof. Outer shield 49 may have spectral protective elements incorporated therein, such as laser protection and/or ultraviolet protection, that are not present in the outer protective spectacle. Thus, when those additional protective elements are deemed desirable, the wearer simply needs to mount the outer shield to the outer protective spectacle. Mounting is readily accomplished by means of clips 50 located at the lower outermost extremities of the outer shield, which clips are adapted to clip onto the corresponding portion of the outer protective spectacle, and retaining member 51, located at and integral with the bridge portion of the outer shield and adapted to retain the bridge portion thereof in close fitting relation with the bridge portion of the outer protective spectacle, generally by interlocking with the corresponding member 52 in the top of the nosepiece (shown in FIG. 5).

It should be readily apparent that any combination of protective elements or treatments may be incorporated into the outer protective spectacle and/or the outer shield and, in some cases, even in the inner spectacle. The selection of protective elements or treatments will vary depending on the types of protection desired in various environments.

The present invention makes it possible to equip a person requiring vision correction with a universal protective spectacle kit that has a variety of protective components included. Once that person has his personal corrective lenses installed in the inner spectacle, he is then able to pick and choose the desired components from his kit to achieve the appropriate protection.

It is contemplated that such a kit would include several nosepieces of various sizes so that a comfortable, good-fitting nosepiece can be attached to the protective spectacle, giving a customized fit for each wearer. It is also contemplated that the kit would include at least two types of outer protective spectacles, perhaps one shaded and one clear, with optional ultraviolet or other protection incorporated therein. One or more outer shields would also be included to provide additional protection against other hazards, for example infra-red or laser radiation.

The protective spectacle of the present invention, and the assembly kit therefor, thus provide a variety of protective options in a mass produced universal package that has not been heretofore available for the eyeglass wearer.

The above description of the invention is illustrative only and is not intended to limit the scope of the invention which is defined by the claims which follow. It should be readily apparent that a variety of equivalent techniques and designs may be utilized to accomplish the same inventive concept illustrated herein, including but not limited to alternative mating relationships between the first and second mounting members, alternative methods for mounting the inner spectacle to the outer protective spectacle, alternative types of nosepiece designs, including those molded as part of the outer protective spectacle, etc.

What is claimed is:

1. A protective spectacle assembly kit comprising:

an impact-resistant, visually transparent protective spectacle adapted to fit the face of a wearer and be retained thereon at eye level so as to substantially protect the eyes of the wearer from projectiles, said impact resistant protective spectacle comprising two frame halves interconnected by a bridge portion;

a discrete nosepiece having locking means for removably snap locking to said impact-resistant protective spectacle;

an outer spectral protective shield having approximately the same size and shape as said impact-resistant protective spectacle, said outer spectral protective shield comprising two frame halves interconnected by a bridge portion; and first mounting means for detachably mounting said outer spectral protective shield to both said nosepiece and said impact resistant protective spectacle.

2. The kit of claim 1 wherein said first mounting means comprises:

a retaining member extending from and being integral with the bridge portion of said outer shield; and an opening in said nosepiece for receiving and retaining said retaining member.

3. The kit of claim 2 wherein said nosepiece has an upper portion and a lower portion and wherein said upper portion has a top surface and wherein:

said opening in said nosepiece is positioned in said top surface of said upper portion.

4. The kit of claim 2 wherein said first mounting means further includes:

a pair of clips located at the lower outermost extremities of said outer shield, said clip being adapted to clip onto the corresponding portion of said impact resistant protective spectacle.

5. The kit of claim 3 wherein said first mounting means further includes:

a pair of clips located at the lower outermost extremities of said outer shield, said clip being adapted to clip onto the corresponding portion of said impact resistant protective spectacle.

6. The kit of claim 1 wherein:

said outer shield provides laser protection or ultraviolet protection.

7. The kit in accordance with claim 1 wherein said locking means comprises:

a clip portion located at and integral with an upper portion of said nosepiece and adapted to clip onto the bridge portion of said outer protective spectacle; and a pair of arms located at a lower portion of said nosepiece and extending downwardly therefrom so as to form an approximately horseshoe shape, said arms having inner surfaces adapted to conform to the shape of the nose of the wearer and having outer surfaces adapted to snugly fit within a nosebridge portion of said outer protective spectacle, said arms further having a small lip extending normal to each of said outer surfaces so as to hold said arms in place within said nosebridge portion, whereby said nosepiece is locked in place by the combined action of said clip portion preventing downward or outward movement of said nosepiece and said lips and said outer surfaces of said arms preventing upward or outward movement of said nosepiece.

8. The kit of claim 7 wherein said first mounting means comprises:

a retaining member extending from and being integral with the bridge portion of said outer shield; and an opening in said nosepiece for receiving and retaining said retaining member.

9. The kit of claim 8 wherein said clip portion has a surface and wherein:

said opening is positioned in said top surface of said clip portion.

10. The kit of claim 1 including:

an inner spectacle adapted to hold corrective lenses, said inner spectacle comprising two frame halves interconnected by a bridge portion; and second mounting means for removably mounting said inner spectacle to said nosepiece such that said inner spectacle, when mounted, is positioned between said impact resistant protective spectacle and the eyes of the wearer in a position to afford approximately optimum visual correction.

11. The kit of claim 10 wherein:

said second mounting means comprises a first mounting member attached to the nosepiece and a corresponding mating second mounting member attached to the bridge portion of said inner spectacle, said first and second mounting members being designed to mate with each other.

12. The kit of claim 11 wherein:

one of said mounting members has a dove-tail shaped groove and the other of said mounting members has a corresponding, mating, dove-tail shaped projection whereby said dove-tail shaped projection slideably, removably mates with said dove-tail shaped groove.

13. The kit of claim 11 wherein:

said frame halves of said inner spectacle are hingedly connected to each other at the bridge portion, thereby allowing said frame halves to fold toward each other and away from said outer protective spectacle.

14. The kit of claim 13 wherein:

said frame halves are hingedly connected to each other through said second mounting member and are biased in the open position.

15. The kit of claim 1 further including:

temple members hingedly attached to opposite outer extremities of said impact resistant protective spectacle and extending rearwardly therefrom to engage the head and ears of said wearer.

16. The kit of claim 15 including:

protective sideshields removably snap-locked to said temple members.

17. The kit of claim 15 including:

a handband removably attached to said temple members.

18. A protective spectacle assembly kit comprising:

an impact-resistant, visually transparent protective spectacle adapted to fit the face of a wearer and be retained thereon at eye level so as to substantially protect the eyes of the wearer from projectiles, said impact resistant protective spectacle comprising two frame halves interconnected by a bridge portion;

a discrete nosepiece having locking means for removably snap locking to said impact-resistant protective spectacle;

an outer spectral protective shield having approximately the same size and shape as said impact-resistant protective spectacle, said outer spectral protective shield comprising two frame halves interconnected by a bridge portion;

first mounting means for detachably mounting said outer spectral protective shield to said nosepiece;

an inner spectacle adapted to hold corrective lenses, said inner spectacle comprising two frame halves interconnected by a bridge portion; and second mounting means for removably mounting said inner spectacle to said nosepiece such that said inner spectacle, when mounted, is positioned between said impact resistant protective spectacle and the eyes of the wearer in a position to afford approximately optimum visual correction.

19. The kit of claim 18 wherein said first mounting means comprises:

a retaining member extending from and being integral with the bridge portion of said outer shield; and an opening in said nosepiece for receiving and retaining said retaining member.

20. The kit of claim 19 wherein said nosepiece has an upper portion and a lower portion and wherein said upper portion has a top surface and wherein:

said opening in said nosepiece is positioned in said top surface of said upper portion.

21. The kit of claim 18 wherein:

said first mounting means further detachably mounts said outer spectral protective shield to said impact resistant protective spectacle.

22. The kit of claim 19 wherein:

said first mounting means further detachably mounts said outer spectral protective shield to said impact resistant protective spectacle.

23. The kit of claim 22 wherein said first mounting means further includes:

a pair of clips located at the lower outermost extremities of said outer shield, said clips being adapted to clip onto the corresponding portion of said impact resistant protective spectacle.

24. The kit of claim 20 wherein said first mounting means further includes:

a pair of clips located at the lower outermost extremities of said outer shield, said clips being adapted to clip onto the corresponding portion of said impact resistant protective spectacle.

25. The kit of claim 18 wherein:

said outer shield provides laser protection or ultraviolet protection.

26. The kit in accordance with claim 18 wherein said locking means comprises:

a clip portion located at and integral with an upper portion of said nosepiece and adapted to clip onto the bridge portion of said outer protective spectacle; and a pair of arms located at a lower portion of said nosepiece and extending downwardly therefrom so as to form an approximately horseshoe shape, said arms having inner surfaces adapted to conform to the shape of the nose of the wearer and having outer surfaces adapted to snugly fit within a nosebridge portion of said outer protective spectacle, said arms further having a small lip extending normal to each of said outer surfaces so as to hold said arms in place within said nosebridge portion, whereby said nosepiece is locked in place by the combined action of said clip portion preventing downward or outward movement of said nosepiece and said lips and said outer surfaces of said arms preventing upward or outward movement of said nosepiece.

27. The kit of claim 26 wherein said first mounting means comprises:

a retaining member extending from and being integral with the bridge portion of said outer shield; and an opening in said nosepiece for receiving and retaining said retaining member.

28. The kit of claim 27 wherein said clip portion has a top surface and wherein:

said opening is positioned in said top surface of said clip portion.

29. The kit of claim 18 wherein:

said second mounting means comprises a first mounting member attached to the nosepiece and a corresponding mating second mounting member attached to the bridge portion of said inner spectacle, said first and second mounting members being designed to mate with each other.

30. The kit of claim 29 wherein:

one of said mounting members has a dove-tail shaped groove and the other of said mounting members has a corresponding, mating, dove-tail shaped projection whereby said dove-tail shaped projection slideably, removably mates with said dove-tail shaped groove.

31. The kit of claim 29 wherein:

said frame halves of said inner spectacle are hingedly connected to each other at the bridge portion, thereby allowing said frame halves to fold toward each other and away from said outer protective spectacle.

32. The kit of claim 31 wherein:

said frame halves are hingedly connected to each other through said second mounting member and are biased in the open position.

33. The kit of claim 18 further including:

temple members hingedly attached to opposite outer extremities of said impact resistant protective spectacle and extending rearwardly therefrom to engage the head and ears of said wearer.

34. The kit of claim 18 including:

protective slideshields removably snap-locked to said temple members.

35. The kit of claim 18 including:

a handband removably attached to said temple members.

* * * * *

UNITED STATES PATENT AND TRADEMARK OFFICE
CERTIFICATE OF CORRECTION

PATENT NO. : 4,810,080

DATED : March 7, 1989

INVENTOR(S) : Clark L. Grendol, et al

It is certified that error appears in the above-identified patent and that said Letters Patent is hereby corrected as shown below:

After column 1, line 3 insert --The Government may have rights in this invention pursuant to Contract No. DAMD17-85-C-5073 awarded by the Department of the Army.--

Signed and Sealed this

Twenty-second Day of September, 1992

Attest:

DOUGLAS B. COMER

Attesting Officer

Acting Commissioner of Patents and Trademarks